(12) United States Patent
Bulan et al.

(10) Patent No.: US 8,153,838 B2
(45) Date of Patent: Apr. 10, 2012

(54) PROCESS FOR PRODUCING ISOCYANATES

(75) Inventors: Andreas Bulan, Langenfeld (DE);
Rainer Weber, Odenthal (DE);
Wolfgang Lorenz, Dormagen (DE);
Gerhard Moormann, Brunsbüttel (DE);
Friedhelm Kämper, Krefeld (DE);
Berthold Keggenhoff, Krefeld (DE)

(73) Assignee: Bayer MaterialScience AG, Leverkusen (DE)

( * ) Notice: Subject to any disclaimer, the term of this patent is extended or adjusted under 35 U.S.C. 154(b) by 60 days.

(21) Appl. No.: 12/164,716

(22) Filed: Jun. 30, 2008

(65) Prior Publication Data

US 2009/0166180 A1  Jul. 2, 2009

Related U.S. Application Data

(63) Continuation of application No. 11/484,253, filed on Jul. 11, 2006, now abandoned.

(30) Foreign Application Priority Data

Jul. 13, 2005  (DE) .................. 10 2005 032 663

(51) Int. Cl.
*C07C 263/00* (2006.01)
(52) U.S. Cl. ........ 560/347; 560/330; 560/336; 560/338; 560/341; 205/620; 204/252; 204/282; 204/290.14
(58) Field of Classification Search .................. None
See application file for complete search history.

(56) References Cited

U.S. PATENT DOCUMENTS

| 5,575,985 | A | * | 11/1996 | Klotz et al. .................. 423/448 |
| 6,149,782 | A | * | 11/2000 | Allen et al. .............. 204/290.14 |
| 6,916,953 | B2 | * | 7/2005 | Walsdorff et al. ............. 560/341 |
| 2004/0069621 | A1 | * | 4/2004 | Gestermann et al. ......... 204/266 |
| 2006/0099138 | A1 | | 5/2006 | Walsdorf et al. |

FOREIGN PATENT DOCUMENTS

| WO | WO-9724320 | 7/1997 |
| WO | WO-0218675 | 3/2002 |
| WO | WO-2004014845 | 2/2004 |
| WO | WO-2004037718 | 5/2004 |
| WO | WO-2006095761 | 9/2006 |

* cited by examiner

*Primary Examiner* — Sudhakar Katakam
(74) *Attorney, Agent, or Firm* — Connolly Bove Lodge & Hutz LLP

(57) ABSTRACT

An isocyanate is produced by:
(a) reacting chlorine with carbon monoxide to form phosgene,
(b) reacting the phosgene with an organic amine to form an isocyanate and hydrogen chloride,
(c) separating the isocyanate and hydrogen chloride,
(d) optionally, purifying the hydrogen chloride,
(e) preparing an aqueous solution of the hydrogen chloride,
(f) optionally, purifying the aqueous solution of hydrogen chloride,
(g) subjecting the aqueous hydrogen chloride solution to electrochemical oxidation to form chlorine, and
(h) returning at least a portion of the chlorine produced in (g) to (a).

25 Claims, No Drawings

PROCESS FOR PRODUCING ISOCYANATES

RELATED APPLICATIONS

This application is a continuation application of U.S. patent application Ser. No. 11/484,253, filed Jul. 11, 2006, which claims priority to German application No. 10 2005 032 663.3, filed Jul. 13, 2005.

BACKGROUND OF THE INVENTION

The present invention is directed to an integrated process for producing isocyanates from phosgene and at least one amine in which chlorine generated by electrochemical oxidation of the hydrogen chloride produced in the course of the phosgenation process is recycled to produce phosgene.

Chlorine is very commonly used as an oxidizing agent in the production chain in the preparation of many organic compounds and in the preparation of raw materials for the production of polymers. Hydrogen chloride is frequently produced as a by-product. For example, chlorine is used in isocyanate production, hydrogen chloride being formed as a by-product. Additional use can be made of the hydrogen chloride, for example by marketing the aqueous solution (hydrochloric acid) or by using it in syntheses of other chemical products. The full amounts of hydrogen chloride that are produced cannot always be marketed or used for other syntheses, however. Furthermore, hydrogen chloride can only be used for syntheses if it has first been purified by appropriate means. On the other hand, its marketing is generally only cost-effective if the hydrogen chloride or hydrochloric acid does not have to be transported over long distances. One of the most common possible uses for the hydrogen chloride that is formed is its use as a raw material in PVC production, wherein ethylene is oxychlorinated with hydrogen chloride to form ethylene dichloride. Disposal of the hydrogen chloride, e.g. by neutralization with alkaline solution, is unappealing from an economic and ecological perspective.

A recycling process for the hydrogen chloride and the return of the chlorine and/or hydrogen to the production process in which the hydrogen chloride is produced is therefore the desired mode of operation. Recycling processes include the catalytic oxidation of hydrogen chloride, by the Deacon process for example, the electrolysis of gaseous hydrogen chloride and the electrolysis of an aqueous solution of hydrogen chloride (hydrochloric acid). Thus an integrated process for producing isocyanates and catalytic oxidation of hydrogen chloride by the Deacon process is disclosed in WO 04/14845, for example, and an integrated process for producing isocyanates and gas phase electrolysis of hydrogen chloride is disclosed in WO 97/24320.

A review of electrochemical recycling processes is given in the article "Chlorine Regeneration from Anhydrous Hydrogen Chloride" by Dennie Turin Mah, published in "$12^{th}$ International Forum Electrolysis in Chemical Industry—Clean and Efficient Processing Electrochemical Technology for Synthesis, Separation, Recycle and Environmental Improvement, Oct. 11-15, 1998, Sheraton Sand Key, Clearwater Beach, Fla".

Catalytic hydrogen chloride oxidation by the Deacon process as a recycling method, as described in WO 04/014845 for example, has a number of processing disadvantages. For instance, the heterogeneously catalyzed hydrogen chloride oxidation can only be adjusted to different load states within certain limits. The Deacon process is markedly more sensitive to load changes than electrolysis. Changing the capacity of an industrial plant for catalytic hydrogen chloride oxidation is also complicated.

A further disadvantage of catalytic hydrogen chloride oxidation is that the catalyst used for the reaction is exceptionally sensitive to impurities in the hydrogen chloride. The recycling capacity falls dramatically due to a loss of activity of the catalyst. At the same time, the lower conversion of hydrogen chloride oxidation in the reactor makes it more difficult to recover the reaction gases emerging from the reactor (oxygen, hydrogen chloride, chlorine, water). Taken as a whole, this reduces the cost-effectiveness of the catalytic oxidation process significantly.

A process is described in WO 97/24320 and EP 876 335 A in which the hydrogen chloride formed during isocyanate production is converted to chlorine by gas phase electrolysis and the chlorine is returned to phosgene production for preparation of the isocyanate. In the special case of the preparation of toluene diisocyanate TDI), hydrogen is also returned to the production of toluene diamine (TDA). The conversion of hydrogen chloride into chlorine by electrolysis in the gas phase has not yet been tried on an industrial scale and has the disadvantage that industrial performance places increased technical demands on the plant components, in terms of their resistance to pressure for example, and is also associated with increased safety costs. A further disadvantage is that if the hydrogen chloride is not completely converted, a further process step has to be performed in which the chlorine that is formed is separated from excess hydrogen chloride. According to EP 1 106 714 A, oxygen is added to the gaseous hydrogen chloride to improve conversion in gas phase electrolysis. The disadvantage here is that with incomplete oxygen conversion, the chlorine that is formed must be freed from hydrogen chloride and additionally from oxygen, by, e.g., total liquefaction.

Furthermore, according to WO 97/24320 and others, so-called solid electrolyte systems, e.g. Nafion® membranes in which the anode and cathode are positioned on either side of the ion-exchange membrane can be used. The anode and cathode can be gas diffusion electrodes, for example. Alternatively, the catalytically active material acting as the anode or cathode can be incorporated into the ion-exchange membrane or applied to the ion-exchange membrane. The disadvantage here is that if the ion-exchange membrane or the catalytically active material is contaminated or damaged, the entire unit, comprising the ion-exchange membrane and the catalytically active material of the electrodes, must be replaced.

The electrochemical oxidation of an aqueous solution of hydrogen chloride using a gas diffusion electrode as the cathode is described for example in WO 00/73538 and WO 02/18675. In these disclosed processes, rhodium sulfide is used as the catalyst for oxygen reduction at the cathode. According to WO 02/18675, this catalyst is largely resistant to organic constituents which can be present in the hydrochloric acid as impurities and which derive from upstream synthesis steps, for example. The organic constituents travel from the anode chamber to the cathode chamber via the ion-exchange membrane. Over an extended electrolysis running time, organic compounds lead to a rise in voltage, which has a negative impact on the cost-effectiveness of the process. In order to remove organic constituents, purification of the hydrochloric acid using activated carbon and optionally additionally using an ion-exchange resin, e.g. a molecular sieve, is proposed in WO 02/18675.

SUMMARY OF THE INVENTION

An object of the present invention is therefore to provide a process for producing isocyanates, with recycling of the hydrogen chloride produced during isocyanate production, which is simple and reliable to operate. In particular, a process which offers rapid start up and shutdown and simple operation under varying load states. Increased capacity should also be easy to achieve.

This and other objects which will be apparent to those skilled in the art are accomplished by electrochemical oxidation of hydrogen chloride generated during phosgenation of an amine to produce chlorine which is then used to produce phosgene for use in a subsequent phosgenation reaction.

DETAILED DESCRIPTION OF THE PRESENT INVENTION

The present invention provides a process for producing isocyanates which includes the following steps:
a) reacting chlorine with carbon monoxide to produce phosgene,
b) reacting phosgene, preferably, the phosgene formed in step (a), with at least one organic amine to form at least one isocyanate and hydrogen chloride,
c) separating and recovering the isocyanates formed in step (b),
d) separating and, optionally, purifying the hydrogen chloride formed in step (b),
e) preparing an aqueous solution of the hydrogen chloride,
f) optionally, purifying the aqueous solution of hydrogen chloride,
g) converting at least a part of the aqueous hydrogen chloride solution by electrochemical oxidation to chlorine, and
h) returning at least a part of the chlorine produced in step (g) to the production of phosgene in step (a).

The process according to the invention is an integrated process for the production of isocyanates and for the electrolysis of an aqueous solution of hydrogen chloride to recover chlorine for the synthesis of phosgene as a starting product for isocyanate production.

In the first step (a) of the process according to the invention, phosgene is produced by reacting chlorine with carbon monoxide. The synthesis of phosgene is known and is described for example in Ullmanns Enzyklopädie der industriellen Chemie, $3^{rd}$ Edition, Volume 13, page 494-500. Other processes for producing isocyanates are described in U.S. Pat. No. 4,764,308 and WO 03/072237, for example. On a technical scale, phosgene is predominantly produced by reacting carbon monoxide with chlorine, preferably on activated carbon as the catalyst. The highly exothermic gas phase reaction takes place at temperatures from at least 250° C. to a maximum of 600° C., generally in multitube fixed-bed reactors. The reaction heat can be dissipated in various ways, for example using a liquid heat-exchanging medium, as described for example in WO 03/072237, or by hot cooling via a secondary cooling circuit with simultaneous use of the reaction heat to generate steam, as disclosed in U.S. Pat. No. 4,764,308, for example.

In step (b), at least one isocyanate is formed from the phosgene produced according to step (a) by reaction with at least one organic amine or a mixture of two or more amines. The process step (b) is also referred to below as phosgenation. The reaction takes place with formation of hydrogen chloride as a by-product.

The synthesis of isocyanates is likewise well known from the prior art, in which phosgene is generally used in a stoichiometric excess, based on the amine. Phosgenation according to (b) conventionally takes place in the liquid phase, wherein the phosgene and the amine can be dissolved in a solvent. Preferred solvents are chlorinated aromatic hydrocarbons, such as chlorobenzene, o-dichlorobenzene, p-dichlorobenzene, trichlorobenzenes, the corresponding chlorotoluenes or chloroxylenes, chloroethylbenzene, monochlorodiphenyl, α- or β-naphthyl chloride, ethyl benzoate, dialkyl phthalate, diisoethyl phthalate, toluene and xylenes. Further examples of suitable solvents are known to those skilled in the art. As is also known from the prior art, e.g. WO 96/16028, the isocyanate which is formed can itself also act as a solvent for phosgene. In another, preferred embodiment, the phosgenation, in particular of suitable aromatic and aliphatic diamines, takes place in the gas phase, i.e. above the boiling point of the amine. Gas phase phosgenation is described in EP 570 799 A, for example. Advantages of this process in comparison with the otherwise conventional liquid phase phosgenation lie in the energy saving due to the minimizing of a complex solvent and phosgene circuit.

In principle, all primary amines having one or more primary amino groups, which can react with phosgene to form one or more isocyanates having one or more isocyanate groups, are suitable as organic amines. The amines have at least one, preferably two, or optionally three or more primary amino groups. Thus aliphatic, cycloaliphatic, aliphatic-aromatic, aromatic amines, diamines and/or polyamines are suitable as organic primary amines. Specific examples of suitable organic primary amines include: aniline; halogen-substituted phenylamines such as 4-chlorophenylamine; 1,6-diaminohexane; 1-amino-3,3,5-trimethyl-5-aminocyclohexane; 2,4-, 2,6-diaminotoluene and mixtures thereof; 4,4'-, 2,4'-, 2,2'-diphenylmethane diamine and mixtures thereof; and also higher-molecular-weight isomeric, oligomeric or polymeric derivatives of such amines and polyamines. Other possible amines are known to those skilled in the art. Preferred amines for the present invention are the amines of the diphenylmethane diamine series (monomeric, oligomeric and polymeric amines); 2,4- and 2,6-diaminotoluene; isophorone diamine and hexamethylene diamine. The corresponding isocyanates, i.e., diisocyanatodiphenyl methane (MDI, monomeric, oligomeric and polymeric derivatives), toluene diisocyanate (TDI), hexamethylene diisocyanate (HDI) and isophorone diisocyanate (IPDI) are obtained during phosgenation.

The amines can be reacted with phosgene in a single-stage, a two-stage or optionally, a multistage reaction. A continuous or discontinuous mode of operation is possible.

If a single-stage phosgenation in the gas phase is chosen, the reaction takes place above the boiling point of the amine, preferably within an average contact time of 0.5 to 5 seconds and at temperatures of from 200 to 600° C.

For phosgenation in the liquid phase, temperatures of from 20 to 240° C. and pressures of 1 to about 50 bar are conventionally used. Phosgenation in the liquid phase can be performed as a single-stage or multistage process in which phosgene may be used in a stoichiometric excess. Here the amine solution and the phosgene solution are combined using a static mixing element and then passed from bottom to top through one or more reaction towers, for example, where the mixture reacts to form the desired isocyanate. In addition to reaction towers, which are equipped with suitable mixing elements, reaction vessels with a stirrer can also be used. As well as static mixing elements, special dynamic mixing elements can also be used. Suitable static and dynamic mixing elements are known to those skilled in the art.

Continuous liquid-phase isocyanate production is generally performed in two stages on an industrial scale. In the first stage, carbamoyl chloride is formed from amine and phosgene and amine hydrochloride from amine and eliminated hydrogen chloride, generally at temperatures of a maximum of 220° C., preferably a maximum of 160° C. This first stage is highly exothermic. In the second stage, the carbamoyl chloride is cleaved to form isocyanate and hydrogen chloride and the amine hydrochloride is reacted to give carbamoyl chloride. The second stage is generally performed at temperatures of at least 90° C., preferably from 100 to 240° C.

After the phosgenation according to step (b), the isocyanates formed during phosgenation are separated off according to the invention in step (c). This is done by first separating the reaction mixture from the phosgenation into a liquid and a gaseous product stream in a manner known to the person skilled in the art. The liquid product stream substantially contains the isocyanate or isocyanate mixture, the solvent and a small amount of unreacted phosgene. The gaseous product stream is substantially composed of hydrogen chloride gas, excess phosgene, and small amounts of solvent and inert gases (e.g., nitrogen and carbon monoxide). The liquid stream from the separation of step (c) then also undergoes processing, preferably distillation, to separate the phosgene and the solvent in succession. A further processing of the isocyanates that are formed optionally also takes place in accordance with step (c). This is done, for example, by fractionating the isocyanate product obtained in a manner known to the person skilled in the art.

The hydrogen chloride obtained from the reaction of phosgene with an organic amine generally contains organic constituents which can disrupt the electrochemical oxidation of an aqueous hydrogen chloride solution according to step (g). These organic constituents include the solvents used in the isocyanate production, such as chlorobenzene, o-dichlorobenzene or p-dichlorobenzene. If electrolysis is carried out by the membrane process, the function of the ion-exchange membrane could be damaged by these organic constituents or by inorganic impurities, such as iron, silicon or aluminum compounds. The impurities can be deposited on the ion-exchange membrane, thereby increasing the voltage of the electrolysis. If a gas diffusion electrode is used as the cathode for the electrolysis, the catalyst of the gas diffusion electrode can also be deactivated by the inorganic or organic impurities. Moreover, these impurities can be deposited on the current collector, thereby diminishing the contact between the gas diffusion electrode and the current collector, leading to a voltage rise. If the diaphragm cell electrolysis process is used for electrolysis of the hydrochloric acid, the cited organic and inorganic constituents can be deposited on the graphite electrodes and/or the diaphragm, thereby increasing the electrolysis voltage.

Accordingly, separation of the hydrogen chloride produced in the phosgenation according to step (b) from the gaseous product stream takes place in a further process step (d). The gaseous product stream which is obtained during separation of the isocyanate according to step (c) is treated in step (d) in such a way that the phosgene can be sent back to the phosgenation reaction and the hydrogen chloride is subjected to an electrochemical oxidation.

The separation of the hydrogen chloride in step (d) is achieved by first separating phosgene from the gaseous product stream. The phosgene is separated by liquefying phosgene, for example at one or more condensers connected in series. The liquefaction preferably takes place at temperatures in the range from −15 to −40° C., depending on the solvent used. Parts of the solvent residues can also be removed from the gaseous product stream through this deep cooling.

Phosgene can additionally or alternatively be washed out of the gas stream in one or more stages with a cold solvent or solvent-phosgene blend. The solvents already used in the phosgenation, chlorobenzene and o-dichlorobenzene, are suitable as solvents for this purpose, for example. The temperature of the solvent or solvent-phosgene blend is generally in the range from −15 to −46° C.

The phosgene separated out of the gaseous product stream can be returned to the phosgenation in step (b). In addition to inert gases such as nitrogen and carbon monoxide, the hydrogen chloride obtained after separation of the phosgene and part of the solvent residue can also contain from 0.1 to 1 wt. % of solvent and from 0.1 to 2 wt. % of phosgene.

A purification of the hydrogen chloride to reduce the proportion of solvent then optionally takes place in accordance with step (d). This can be done by freezing, for example, by passing the hydrogen chloride through one or more cryogenic traps, depending on the physical properties of the solvent.

In a preferred embodiment, the hydrogen chloride is purified by passing it through two heat exchangers connected in series, in which the solvent to be removed is frozen out at −40° C., for example, depending on the fixed point. The heat exchangers are run alternately, so that the heat exchanger through which the gas stream first passes thaws out the previously frozen solvent. The solvent can be reused to produce a phosgene solution. In the second heat exchanger connected downstream, which contains a conventional heat-exchanging medium for refrigerating machines, e.g. a compound from the series of freons, the gas is cooled to below the fixed point of the solvent so that the latter crystallizes out. At the end of the thawing and crystallization process, the gas stream and the refrigerant stream are switched so that the function of the heat exchanger is reversed. In this way the gas stream containing hydrogen chloride can be depleted to a solvent content of preferably a maximum of 500 ppm, more preferably a maximum of 50 ppm, most preferably a maximum of 20 ppm.

Alternatively, purification of the hydrogen chloride can take place in two heat exchangers connected in series, as described in U.S. Pat. No. 6,719,957. Here the hydrogen chloride is compressed to a pressure of 5 to 20 bar, preferably 10 to 15 bar, and the compressed gaseous hydrogen chloride is passed to a first heat exchanger at a temperature of 20 to 60° C., preferably 30 to 50° C. The hydrogen chloride is cooled with cold hydrogen chloride at a temperature of −10 to −30° C., which comes from a second heat exchanger. Organic constituents condense in this process and can be sent for disposal or recycling. The hydrogen chloride supplied to the first heat exchanger leaves it at a temperature of −20 to −0° C. and is cooled in the second heat exchanger to a temperature of −10 to −30° C. The condensate formed in the second heat exchanger is composed of additional organic constituents and small amounts of hydrogen chloride. To avoid a loss of hydrogen chloride, the condensate discharged from the second heat exchanger is sent to a separation and evaporator unit. This can be a distillation column, for example, in which the hydrogen chloride is stripped from the condensate and returned to the second heat exchanger. The stripped hydrogen chloride can also be returned to the first heat exchanger. The hydrogen chloride cooled in the second heat exchanger and freed from organic constituents is passed to the first heat exchanger at a temperature of from −10 to −30° C. After being heated to 10 to 30° C., the hydrogen chloride freed from organic constituents leaves the first heat exchanger.

In an alternative process, the purification of the hydrogen chloride optionally provided according to step (d) takes place by adsorption of organic impurities, such as solvent residues, on activated carbon. Here, after removal of excess phosgene at a pressure of from 0 to 5 bar, preferably 0.2 to 2 bar, the hydrogen chloride is passed over or through an activated carbon bed, for example. The flow rates and residence times are adjusted to the content of impurities in a manner known to the person skilled in the art. The adsorption of organic impurities is just as possible on other suitable adsorbents, such as zeolites.

In a further alternative process, the hydrogen chloride can be purified by distillation. This takes place after condensation of the gaseous hydrogen chloride. In the distillation of the condensed hydrogen chloride, the purified hydrogen chloride is removed as the overhead product of the distillation, the distillation taking place under the conventional conditions of pressure, temperature, etc., for such a distillation known to the person skilled in the art.

In step (e), an aqueous hydrogen chloride solution is prepared from the hydrogen chloride separated off and optionally purified in step (d). To this end, the hydrogen chloride is preferably sent for adiabatic hydrogen chloride absorption, which takes place in an absorption column with addition of a suitable absorbent. In a preferred embodiment, the absorbent is an aqueous hydrogen chloride solution (hydrochloric acid) in the concentration range up to 20 wt. %, preferably 16 to 18 wt. %. Alternatively, a hydrochloric acid of a lower concentration or deionized water or a steam condensate can also be used. The adiabatic absorption of hydrogen chloride in aqueous hydrochloric acid to produce concentrated hydrochloric acid is already known from the prior art The absorption takes place, for example, by introducing the stream of hydrogen chloride into the lower section of an absorption column, the absorption column being equipped with material exchange elements, such as sieve plates or packing. The absorbent is introduced into the upper section of the absorption column, above the material exchange elements. The hydrogen chloride gas is absorbed, i.e. dissolved, countercurrently at the material exchange elements in the absorbent.

In the conventional process temperature range of from 90 to 120° C., preferably 105 to 109° C., the gas stream (i.e., the vapors) emerging at the head of the absorption column is substantially made up of water vapor. In addition, hydrogen chloride, inert gases such as nitrogen and carbon monoxide, phosgene which has not yet reacted with water and residual amounts of solvent are still included. To separate off condensable components, such as water, hydrochloric acid and solvent residues, and to dissipate the heat of condensation, the gaseous overhead stream is preferably passed to a condensation unit. This condensation unit can be made up of one or more shell-and-tube heat exchangers connected in series and run on cooling water, for example. The liquid runoff from this condensation system is then preferably sent to a separator to separate off the condensed-out solvent components from the aqueous hydrochloric acid phase. This separator is preferably a static phase separator. The separation of the organic and aqueous phase can be supported by corresponding separating elements in this separator. The separated organic phase is sent for appropriate recovery. The solvent-depleted hydrochloric acid phase can be returned to the upper section of the absorption column.

The aqueous hydrogen chloride solution (hydrochloric acid) leaving the lower section of the absorption column can, if necessary, be cooled with a suitable cooler, optionally purified according to step (f) and then sent for electrochemical oxidation in accordance with step (g). This solution is generally about 24 to 30 wt. %, preferably 27 to 30 wt. % hydrochloric acid (also referred to below as concentrated hydrochloric acid) and contains solvent proportions of preferably a maximum of 0.05 wt. %, most preferably a maximum of 0.005 wt. %. The phosgene content of the hydrochloric acid is preferably from about 0.1 to 0.0001 wt. %, but can also be less than 0.0001 wt. %.

The aqueous hydrogen chloride solution optionally undergoes a purification in a step (f), in particular to further reduce the solvent proportion and the phosgene content. This can take place by stripping in a column in a manner known to the person skilled in the art, for example, by introducing the concentrated hydrochloric acid into a packed column which is fitted with either a circulation evaporator or a steam inlet. While the vapors from the stripper column can be returned to the absorption column, the liquid output from the column in the form of purified concentrated hydrochloric acid can be sent for hydrochloric acid electrolysis according to step (g), optionally via a cooler. Instead of carrying out the stripping in a separate stripper column, it can also take place in the absorption column itself by direct injection of steam, preferably in the stripping section located below the absorption column. Instead of stripping in the absorption column, the solvent content in the hydrogen chloride can also be reduced by partial distillation with the aid of a heat exchanger connected downstream from the absorption column.

In optional step (f), the aqueous hydrogen chloride solution undergoes a purification to remove iron, aluminum and/or silicon compounds. The removal of iron, aluminum and/or silicon compounds preferably takes place using chelating ion exchangers. Such ion exchangers are available commercially.

Thus the removal of iron compounds, for example, can be accomplished by using ion exchangers such as those which are commercially available under the name Amberjet 4400CI from Rohm & Haas or Lewatit M500 from LANXESS. The concentration of hydrochloric acid for removal of iron is preferably at least 8 wt. %.

Precipitation in the form of poorly soluble compounds and subsequent filtration can also be used to remove iron-containing compounds.

After preparing an aqueous hydrogen chloride solution according to step (e) and optionally after purification of the aqueous hydrogen chloride solution according to step (f), the hydrochloric acid is passed to an electrolytic cell. The electrochemical oxidation of the hydrochloric acid according to step (g) can be performed by the membrane process or by the diaphragm cell electrolysis process in a two-chamber electrolytic cell composed of an anode chamber and a cathode chamber or in a three-chamber electrolytic cell composed of an anode chamber, a cathode chamber and an electrolyte chamber between the anode and cathode chamber. A two-chamber electrolytic cell is preferred. In the membrane process, the anode chamber is separated from the cathode chamber by an ion-exchange membrane (also simply referred to below as a membrane), in particular a cation-exchange membrane. In the diaphragm cell electrolysis process, the anode chamber is separated from the cathode chamber by a diaphragm. The distance of the electrodes (anode and cathode) from the diaphragm or membrane is preferably from 0 to 3 mm, more preferably from 0 to 2 mm. Suitable ion-exchange membranes are available commercially. One such suitable single-layer ion-exchange membrane with sulfonic acid groups is a Nafion® 117 membrane which is commercially available from DuPont.

As the diaphragm, a woven diaphragm according to DE 3 321 159 A can be used, for example. Plastic threads can be used for this. Polyvinyl chloride (PVC) or polyvinylidene fluoride (PVDF) fabrics, or mixed fabrics with PVC and PVDF threads are examples of thread materials which can be used to make suitable woven diaphragms. Warp or weft threads can be made up of multifilament threads, as described in DE 3 321 159 A, as well as monofilament threads. After the diaphragm has been woven, the fabric can be compressed, e.g. by calendering, to optimize the gas permeability.

Electrodes containing graphite, the anode and/or the cathode preferably being substantially of graphite, can be used in the electrolysis of hydrochloric acid by the diaphragm cell electrolysis process or the membrane process. Bipolar graphite electrodes are most preferably used. According to DE 4 417 744 A, a particularly advantageous design of cathode and/or anode is a graphite cathode and/or anode with a noble metal-containing coating, for example, an iridium-containing coating.

The graphite anodes have in particular a geometrical shape, as is known from DE 3 041 897 A. The cathodes preferably have a similar structure to the anodes. The shape of the anode and/or cathode preferably exhibits vertically arranged grooves, flutes, notches, or indentations. These grooves substantially serve to carry off the gas which is formed during electrolysis, i.e. chlorine and hydrogen, upwards out of the narrow gap between the electrode and the diaphragm or membrane. The grooves preferably have a depth of 5 to 35 mm, most preferably 15 to 25 mm, and a width of preferably 1 to 5 mm. The distance between two adjacent grooves substantially positioned parallel to each other is generally from 4 to 6 mm. In another embodiment, the depth and/or width of the grooves varies along their length. Thus the depth of the grooves can be from 12 to 15 mm at the lower end of the grooves and from 20 to 30 mm at the upper end of the grooves.

Hydrochloric acid is used as the electrolyte in both the anode chamber and the cathode chamber. During electrolysis, chlorine is produced at the anode, hydrogen at the cathode.

A preferred mode of operation of the electrochemical oxidation of hydrochloric acid involves adding metal ions from the group of platinum metals, preferably platinum and/or palladium, to the hydrochloric acid which serves as the electrolyte in the cathode chamber. Solutions of hexachloroplatinate(IV) acid ($H_2PtCl_6$) or solutions of disodium tetrachloropalladate(II) ($Na_2PdCl_4$) or mixtures thereof can thus be added, for example. The addition can take place continuously or discontinuously. The addition of metal ions to the hydrochloric acid in the cathode chamber serves to maintain a low electrolysis voltage in the range from 1.6 to 2.1 V, compared with 2.2 to 2.3 V without addition of metal ions, at 5 kA/m$^2$ and 70 to 80° C. and with a preferably 15 to 25%, more preferably approx. 20%, hydrochloric acid. A quantity of metal ions is which is sufficient to maintain the electrolysis voltage in the range from 1.8 to 2.1 is generally added. This means that the addition of metal ions is increased as the electrolysis voltage rises during operation.

The electrolysis of step (g) is preferably performed at a temperature of from 50 to 90° C. The concentration of the aqueous solution of hydrogen chloride that is used is preferably 15 to 25 wt %. The electrolysis can be performed at an absolute pressure of 1 bar or at a higher pressure of up to 2 bar. Higher pressures are generally possible but require a correspondingly greater complexity in the design of the electrolytic cell. The differential pressure between the anode chamber and the cathode chamber is preferably 0 to 10 mbar, most preferably approx. 1 mbar, so that, due to the higher pressure on the anode side, traces of the chlorine gas that is formed pass through the diaphragm to the cathode side and can therefore mix with the hydrogen formed at the cathode.

In an alternative embodiment, the electrochemical oxidation of the aqueous solution of hydrogen chloride in step (g) is conducted by the membrane process with a gas diffusion electrode as the cathode. In this case, the electrolytic cell can be composed either of two chambers or of three chambers, but preferably two chambers. An oxygen-containing gas, e.g. oxygen, air or oxygenated air, is supplied to the cathode half cell. The oxygen is reduced at the gas diffusion electrode, forming water. The aqueous hydrogen chloride solution is supplied to the anode half cell, the hydrogen chloride being oxidized to chlorine at the anode. The anode half cell and the cathode half cell are separated from each other by a cation-exchange membrane. The electrolysis of hydrochloric acid using a gas diffusion electrode as the cathode is described in WO 00/73538, for example.

The electrolytic cell can be made up of either a non-metallic material (disclosed, e.g., in DE 103 47 703 A) or a metallic material. Titanium or a titanium alloy, such as a titanium-palladium alloy, is a suitable metallic material for the electrolytic cell. In this case, the shells for the anode and cathode half cell, the current distributor and the supply leads are made from titanium or a titanium alloy.

The anode can be designed in accordance with DE 102 34 806 A, for example. In this case, the anode is composed of a metal (preferably titanium) with a coating of noble metal oxide (e.g., ruthenium oxide). Furthermore, in accordance with DE 102 00 072 A, the titanium anode can have an interlayer of titanium carbide or titanium boride, which is applied to the titanium anode by plasma spraying or flame spraying before the noble metal oxide coating is applied. According to DE 102 34 806 A, the metal anode has openings for the passage of the gas formed during electrolysis, the openings preferably having guide structures which lead the gas that is formed to the side of the metal anode facing away from the ion-exchange membrane. Here the total cross-sectional area of the openings should be in the range from 20% to 70% of the area which is formed by the height and width of the anode. The metal anode can moreover have an undulated, zigzag or rectangular cross-section. The depth of the anode should be at least 1 mm. The ratio of electrochemically active area of the metal anode to the area formed by the height and width of the metal electrode should be at least 1.2. In a special embodiment, the metal anode can be made up of two adjacent expanded metal meshes, the expanded metal mesh facing the ion-exchange membrane having a finer structure than the expanded metal mesh facing away from the ion-exchange membrane. Furthermore, the more finely structured expanded metal mesh is rolled flat and the more coarsely structured expanded metal mesh is positioned so that the mesh strands are inclined towards the cathode and serve as guide structures. Alternatively, the anode can also be made up of an expanded metal mesh. In principle, the anode should have a free surface area of from 15 to 70%. The thickness of the expanded metal meshes should be chosen so that no additional electrical resistance occurs with a bipolar connection of the individual electrolytic cells (cell elements) to an electrolyzer. The electrical resistance substantially depends on the electrical contacting of the anode, such as the number of current-supplying connecting elements between the anode and the back wall of the anode half cell.

In the case of electrolysis using a gas diffusion electrode, the anode chamber and cathode chamber can be separated by a commercial ion-exchange membrane. Nafion® 324 or Nafion® 117 ion-exchange membranes from DuPont can be used, for example. A membrane is preferably used which, as described in WO 05/12596, has a smooth surface texture on the side facing the gas diffusion electrode. The smooth surface texture of the membrane allows the gas diffusion electrode and the membrane to lie against each other in such a way that under a pressure of 250 g/cm$^2$ and at a temperature of 60° C. the contact area is at least 50% of the geometrical surface area of the membrane.

The cathodic current distributor to which the gas diffusion electrode is applied is preferably designed in accordance with DE 102 03 689 A. This has a free surface area of less than 65% but more than 5%. The thickness of the current distributor is at least 0.3 mm. It can be composed of an expanded metal mesh, lattice, woven fabric, foam, nonwoven fabric, slotted plate or perforated plate made from metal. The cathodic current distributor is preferably an expanded metal mesh with a mesh length of 4 to 8 mm, a mesh width of 3 to 5 mm, a strand width of 0.4 to 1.8 mm and a thickness of 0.4 to 2 mm. The cathodic current distributor can additionally have a second expanded metal mesh as a support for the first expanded metal mesh. The second expanded metal mesh as the support preferably has a mesh length of 10 to 40 mm, a mesh width of 5 to 15 mm, a strand width of 2 to 5 mm and a thickness of 0.8 to 4 mm. A lattice which preferably has a wire thickness of 1 to 4 mm and a mesh size of 7 to 25 mm can also be used as a support. Furthermore, a perforated plate or slotted plate which preferably has an open area of less than 60% and a thickness of 1 to 4 mm can be used as a support. Titanium or a noble metal-containing titanium alloy, such as titanium-palladium, can be used as the material for the cathodic current distributor. If the current distributor is an expanded metal mesh, it is preferably rolled.

A commercial gas diffusion electrode equipped with a suitable catalyst can be used as the gas diffusion electrode. According to WO 00/73538, suitable catalysts contain rhodium and/or at least one rhodium sulfide or a mixture of rhodium and at least one rhodium sulfide. According to EP 931 857 A, rhodium and/or rhodium oxide or mixtures thereof can also be used. The gas diffusion electrode is preferably composed of an electrically conductive woven fabric, paper or nonwoven fabric made from carbon with the woven fabric, paper or nonwoven fabric having a carbon-containing catalyst layer on one side and a gas diffusion layer on the other side. The catalysts preferably applied to a support, preferably composed of carbon in which polytetrafluoroethylene particles are integrated. The gas diffusion layer is preferably composed of carbon and polytetrafluoroethylene particles, the ratio of carbon to PTFE being 50:50, for example. The gas diffusion electrode can be positioned so that it is not permanently connected to the ion-exchange membrane. The contacting of the gas diffusion electrode with the current distributor and the ion-exchange membrane is preferably made by press contact, i.e. the gas diffusion electrode, the current distributor and the membrane are pressed against one another. The gas diffusion electrode can be connected to the current collector as described in DE 101 48 600 A.

The electrolysis of hydrochloric acid by the membrane process with a gas diffusion electrode is conventionally performed at a temperature of from 40 to 70° C. The concentration of the aqueous solution of hydrogen chloride in the anode chamber is from 10 to 20 wt. %, preferably 12 to 17 wt. %. The cell can be operated, for example, in such a way that the pressure in the anode chamber is higher than the pressure in the cathode chamber. In this way, the cation-exchange membrane is pressed against the gas diffusion electrode and this in turn is pressed against the current distributor. Alternatively, an electrolytic cell design as described in DE 101 38 214 A can be chosen. The anode and/or the current distributor are elastically supported, for example by being connected by springs to the back wall of the relevant half cell. A so-called zero gap configuration occurs when the cell is assembled, wherein the anode is in direct contact with the ion-exchange membrane, which in turn is in direct contact with the gas diffusion electrode and this in turn is in direct contact with the current distributor. The elastic support causes the anode, membrane, gas diffusion electrode and current distributor to be pressed together.

In a preferred embodiment of the electrolysis process, when the electrolytic cell according to DE 10 152 275 A is started, the anode half element is filled with a 5 to 20 wt. % hydrochloric acid, the hydrochloric acid containing at least 10 ppm of free chlorine and the concentration of the hydrochloric acid during startup being more than 5 wt. %. The volumetric flow rate of the hydrochloric acid through the anode chamber is adjusted so that at the start of electrolysis, the hydrochloric acid in the anode chamber flows at a rate of 0.05 to 0.15 cm/s. The electrolysis is started with a current density of 0.5 to 2 kA/m$^2$ and increased in time intervals of 5 to 25 minutes by 0.5 to 1.5 kA/m$^2$ each time. Once a predefined current density of preferably 4 to 7 kA/m$^2$ is reached, the volumetric flow rate of the hydrochloric acid is adjusted so that the hydrochloric acid in the anode half element flows at a rate of 0.2 to 0.4 cm/s.

A particularly advantageous mode of operation of the electrolytic cell can take place in accordance with DE 101 38 215 A which teaches operation of the electrolytic cell with an elevated pressure in the cathode chamber to lower the cell voltage. The differential pressure between the anode chamber and cathode chamber should be 0.01 to 1000 mbar and the oxygen pressure in the cathode chamber at least 1.05 bar absolute.

In accordance with the present invention, in process step (h), at least a part of the chlorine produced in step (g) is returned to phosgene production in step (a). Before being returned, the chlorine is preferably cooled in a single-stage or multistage cooling process by means of a cooler, e.g. a tubular heat exchanger, and dried. Drying can take place with the aid of a suitable desiccant in an absorption column equipped with material exchange elements, for example. In addition to molecular sieves or hygroscopic adsorbents, a suitable desiccant can be sulfuric acid for example, as described e.g. in DE 10 235 476. Drying can take place in one or more stages. Drying preferably takes place in two stages, by bringing the chlorine to be dried into contact in a first stage with a sulfuric acid of reduced concentration, preferably 70 to 80%, most preferably 75 to 80%. In a second stage, the residual moisture is removed from the chlorine by means of a more highly concentrated sulfuric acid of preferably 88 to 96%, most preferably 92 to 96%. The chlorine dried in this way having a residual moisture of preferably a maximum of 100 ppm, more preferably a maximum of 20 ppm, can be passed through a droplet separator to remove any sulfuric acid droplets still remaining therein.

The circulatory mode of operation of the process of the present invention requires addition of chlorine in addition to the chlorine produced by electrolysis in step (g) to the phosgene production in step (a), because losses of chlorine and hydrogen chloride occur in the chlorine-hydrogen chloride circuit. A portion of the added chlorine can be in the form of elemental chlorine from an external source, for example the electrolysis of an aqueous sodium chloride solution. The losses of chlorine and hydrogen chloride that occur can, however, also be balanced out by providing a portion of hydrogen chloride from an external source. A portion of hydrogen chloride in the form of an aqueous hydrogen chloride solution from an external source (e.g., from a production process in which an aqueous hydrogen chloride solution is produced as a by-product) is preferably supplied as an approx. 30 wt. % hydrochloric acid in step (e) to produce the aqueous hydrogen chloride solution for electrolysis in step (g). A hydrochloric acid of lower concentration can alternatively be supplied to the absorption of hydrogen chloride according to step (e).

If the missing amount is replaced by chlorine, this chlorine, which is produced by rock salt electrolysis, for example, may contain small amounts of bromine or iodine. If this chlorine is used for the production of MDI, a discoloration of the polyurethane products produced from MDI can occur with a certain concentration of bromine and iodine compounds, as described for example in DE 10 235 476 A. By contrast, the chlorine returned to the process according to the invention is largely free from bromine and iodine, so that a certain proportion of bromine and iodine in the chlorine supplied from outside to the recycled chlorine may be present. A preferred embodiment of the process according to the invention thus involves using some chlorine from a source other than the electrochemical oxidation of the process of the present invention in the production of phosgene to be used for TDA phosgenation, while the low-bromine and low-iodine chlorine from the electrolysis according to step (g) is used in the production of phosgene for the phosgenation of MDA (diphenylmethane diamine). In the production of TDI by phosgenation of TDA, bromine and iodine are bound in the TDI and are thus removed from the hydrogen chloride circuit. During recovery of TDI by distillation, bromine and iodine are separated from the TDI, however, and remain in the residue.

In another preferred embodiment of the process of the present invention, the carbon monoxide used in the production of phosgene according to step (a) is produced by reacting methane with water in a steam reformer and reacting the hydrogen produced in that process with at least one organic nitro compound to form at least one amine, which is used in the production of the isocyanate according to step (b). The production of carbon monoxide by reacting methane with water in a steam reformer has long been known. The reaction of hydrogen with an organic dinitro compound to produce an amine (hydrogenation) is likewise known. If a steam reformer is used to produce carbon monoxide, the stoichiometrically required amount of carbon monoxide for phosgene production and the stoichiometric amount of hydrogen for hydrogenation of the dinitro compounds are available. Nitrobenzene and dinitrotoluene (DNT) can be used as the nitro compounds, for example. Nitrobenzene and dinitrotoluene are hydrogenated to form aniline and toluene diamine (TDA). Aniline is processed further to produce polyamines of the diphenylmethane series. In addition to other amines, MDA and TDA can be used for isocyanate production according to step (c). An assessment of the cost-effectiveness of the overall process for producing isocyanates also includes the production of carbon monoxide, the carbon monoxide preferably being produced from natural gas in a steam reformer. If other reformer processes are used, e.g. coal gasification or cracking of petroleum fractions, different ratios of carbon monoxide to hydrogen are obtained. The higher the ratio of carbon monoxide to hydrogen, the less cost-effective the overall process, since the missing hydrogen for hydrogenation of the dinitro compound to form the homologous diamines has to be supplied from another source. The missing hydrogen can be provided by the electrolysis of hydrochloric acid by the diaphragm cell electrolysis process, for example.

The advantages of the integrated process of the present invention for producing isocyanates with electrochemical oxidation of an aqueous solution of the hydrogen chloride produced during isocyanate production to recover chlorine for the synthesis of phosgene lie in the fact that the electrochemical oxidation can be operated more simply than a catalytic oxidation by the Deacon process. The simpler operation relates to the startup and shutdown of the electrolytic cells and the adjustment to variable load states and to a higher or lower capacity of the plant. Furthermore, the electrochemical oxidation of an aqueous solution of hydrogen chloride can be operated more simply than a gas phase electrolysis of hydrogen chloride, since the process is performed not in the gas phase but with a solution.

Through the production of a concentrated hydrochloric acid of about 30% from a hydrochloric acid of about 17% in step (f), the production of isocyanates in conjunction with the electrochemical oxidation of hydrochloric acid also offers the possibility of removing concentrated hydrochloric acid from the circuit for other applications if required. One possible use of this concentrated hydrochloric acid lies in the food sector. For this purpose, a sufficiently high purity for the food industry can be achieved for the concentrated hydrochloric acid produced by the process according to the invention, e.g. by absorptive post-purification on an activated carbon bed, as is known from the prior art. Additionally, the concentrated hydrochloric acid may be used as a catalyst in the production of MDA. The production of polyamines of the diphenylmethane series conventionally takes place by reacting aniline and formaldehyde in the presence of acid catalysts, as is common knowledge from the prior art. Hydrochloric acid is conventionally used as the acid catalyst.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

EXAMPLE

This example uses as a starting material hydrogen chloride gas which still contains phosgene and has been obtained from an MDI production process after the MDI has been removed.

After removing phosgene from the HCl gas, 44,660 kg/h of HCl are compressed to 13.4 bar, the temperature of the HCl is about 40° C., the content of monochlorobenzene (MCB) is 200 ppm and the content of orthodichlorobenzene (ODB) is 70 ppm. This HCl stream is passed to a first heat exchanger and cooled to about −9.2° C. In this process a portion of the hydrogen chloride is condensed out together with ODB and MDB. This portion of about 62 kg/h, of which the temperature is −9.2° C., is passed to a separator/evaporator unit. The purified residual stream of 44,598 kg/h is passed to a second heat exchanger, where it is cooled to −23.4° C. During this cooling a partial stream of hydrogen chloride containing the impurities MCB, ODB and possible other high-boiling components is again condensed out. This partial stream is 998 kg/h and is passed to the separator/evaporator unit. The remaining twice-purified residual HCl stream of 44,573 kg/h and −23.4° C. is recycled to the first heat exchanger for cooling the abovementioned crude HCl gas stream and is heated therein to about 21° C. and then passed for HCl absorption in water. The heated HCl stream issuing from the first heat exchanger has an MCB and ODB content of less than 1 ppm.

The HCl partial streams (62 mg/h and 998 kg/h) from the first and second heat exchangers are passed to a separator/evaporator unit for freeing hydrogen chloride from impurities (the high-boiling components). 87 kg/h of HCl of a temperature of about −12.2° C. are discharged from the separator/evaporator unit and the remaining quantity of 973 kg/h is passed to the second heat exchanger. The separator/evaporator unit can for example be a distillation column with an evaporator at the base of the column.

The twice purified hydrogen chloride is absorbed in water, as described, whereupon 30% hydrochloric acid is produced.

The 30% hydrochloric acid is passed to hydrochloric acid electrolysis in which an oxygen depletion cathode is used as the cathode. The anode and cathode chambers of the electrolysis are separated by an ion exchanger membrane from DUPONT Nafion 324. The temperature of the anolyte is 50° C. and the current density is 5 kA/m² at an electrolysis voltage of 1.39V. The anode consists of titanium which is provided with a noble metal coating from DENORA. The oxygen depletion cathode used is a rhodium sulphide-containing gas diffusion electrode from ETEK, which rests on a current distributor of titanium which is stabilized with palladium. The differential pressure between the anode chamber and the cathode chamber is adjusted so that the membrane is pressed on the oxygen depletion cathode and the current distributor. The differential pressure is 200 mbar. The electrolytic cell is operated at an absolute pressure of 1.01 bar. The anode chambers of the electrolysis are charged with 1466 t/h of hydrochloric aicd of a concentration of 14% by weight and hydrochloric acid of a concentration of 12.2% by weight is removed from the anode chambers. A purging stream of 96 t/h of 12.2% by weight hydrochloric acid is continuously removed and the remaining current is strengthened with 148.5 t/h of the purified 30% hydrochloric cid and recycled to the electrolysis.

32.4 t/h of chlorine are able to be removed from the anode chambers.

1.2 mol of water are transported through the membrane per mol of proton, so that 19.7 t/h of water enter the cathode chamber through the membrane. In this chamber this water is removed together with the reaction water from the oxygen reduction in the form of a condensate. 28.1 t/h of condensate containing 0.8% by weight of HCl are obtained. 7.29 t/h of pure oxygen are introduced into the cathode chambers.

What is claimed is:

1. A process for the production of an isocyanate comprising:
   (a) reacting chlorine with carbon monoxide to produce phosgene,
   (b) reacting the phosgene formed in (a) with at least one organic amine to form an isocyanate and hydrogen chloride,
   (c) separating the isocyanate from the hydrogen chloride,
   (d) optionally, purifying the hydrogen chloride,
   (e) preparing an aqueous solution of the hydrogen chloride,
   (f) purifying the aqueous solution of hydrogen chloride to a content of organic solvents of a maximum of 0.05 wt. %, wherein the purification is carried out by stripping the aqueous hydrogen chloride solution with steam,
   (g) subjecting at least a portion of the aqueous hydrogen chloride solution to electrochemical oxidation to form chlorine, and
   (h) returning at least a portion of the chlorine produced in (g) to (a).

2. The process of claim 1 in which phosgene is separated from the hydrogen chloride in (d) by liquefaction.

3. The process of claim 1 in which the hydrogen chloride is purified in (d) by freezing.

4. The process of claim 1 in which the aqueous hydrogen chloride solution formed in (e) is formed by absorption in an aqueous solution of hydrogen chloride having a concentration of 15 to 20 wt. %.

5. The process of claim 1 in which purification in (f) is carried out with a chelating ion exchanger to remove iron, silicon and/or aluminum compounds from the aqueous hydrogen chloride solution.

6. The process of claim 5 in which the aqueous hydrogen chloride solution is an at least 8 wt. % solution.

7. The process of claim 1 in which (g) is carried out in an electrolytic cell having an anode chamber and a cathode chamber separated by an ion-exchange membrane.

8. The process of claim 1 in which (g) is carried out in an electrolytic cell having an anode chamber and a cathode chamber separated by a diaphragm.

9. The process of claim 7 in which the anode and/or the cathode comprise graphite.

10. The process of claim 9 in which the cathode comprises graphite and has a coating which contains iridium.

11. The process of claim 9 in which the anode and/or cathode has vertically arranged grooves.

12. The process of claim 8 in which the anode and/or cathode comprise graphite.

13. The process of claim 12 in which the cathode comprises graphite and has a coating which comprises iridium.

14. The process of claim 8 in which the anode and/or cathode has vertically arranged grooves.

15. The process of claim 1 in which platinum group metal ions are added to the aqueous hydrogen chloride solution before (e).

16. The process of claim 1 in which platinum and/or palladium ions are added to the aqueous hydrogen chloride solution before (e).

17. The process of claim 1 in which a gas diffusion electrode is used as cathode in (g).

18. The process of claim 17 in which the gas diffusion electrode comprises an electrically conductive woven fabric, an interwoven fabric, a knitted fabric, a lattice or a non-woven fabric made from carbon which is positioned between a carbon-containing catalyst layer and a gas diffusion layer.

19. The process of claim 18 in which the catalyst layer comprises rhodium, a rhodium sulfide or a mixture of rhodium and a rhodium sulfide.

20. The process of claim 1 in which an anode comprising titanium and having a coating of at least one noble metal oxide is used in (g).

21. The process of claim 1 in which an anode comprising titanium and having a ruthenium oxide coating is used in (g).

22. The process of claim 1 in which an electrolytic cell comprising a titanium and/or a titanium alloy is used in (g).

23. The process of claim 1 in which (i) the carbon monoxide used in (a) is produced by reacting methane with water in a steam reformer, (ii) hydrogen produced during the reaction of water with methane is reacted with an organic nitro compound to form an amine, and (iii) the amine produced in (ii) is used in (b).

24. The process of claim 1 in which chlorine containing bromine and/or iodine is used in (a) to form phosgene which is reacted with TDA in (b).

25. A process for the production of an isocyanate comprising:
   (a) reacting chlorine with carbon monoxide to produce phosgene,
   (b) reacting the phosgene formed in (a) with at least one organic amine to form an isocyanate selected from the group consisting of diisocyanatodiphenyl methane (MDI) and toluene diisocyanate (TDI) and hydrogen chloride,
   (c) separating the isocyanate from the hydrogen chloride,
   (d) optionally, purifying the hydrogen chloride,
   (e) preparing an aqueous solution of the hydrogen chloride,
   (f) purifying the aqueous solution of hydrogen chloride to a content of organic solvents of a maximum of 0.05 wt. %, wherein the purification is carried out by stripping the aqueous hydrogen chloride solution with steam,
   (g) subjecting at least a portion of the aqueous hydrogen chloride solution to electrochemical oxidation to form chlorine, and
   (h) returning at least a portion of the chlorine produced in (g) to (a) and mixing it with raw chlorine.

* * * * *